United States Patent [19]

Kumakura et al.

[11] Patent Number: 4,769,082
[45] Date of Patent: Sep. 6, 1988

[54] METHOD OF PRETREATMENT IN SACCHARIFICATION AND FERMENTATION OF WASTE CELLULOSE RESOURCE

[75] Inventors: Minoru Kumakura; Noboru Kasai; Masao Tamada; Isao Kaetsu, all of Gunma, Japan

[73] Assignee: Japan Atomic Energy Research Institute, Tokyo, Japan

[21] Appl. No.: 33,854

[22] Filed: Mar. 27, 1987

Related U.S. Application Data

[63] Continuation of Ser. No. 778,087, Sep. 20, 1985, abandoned.

[30] Foreign Application Priority Data

Sep. 25, 1984 [JP]   Japan .................................. 59-199779

[51] Int. Cl.⁴ ........................... C13K 1/02; C12P 7/08; C08B 1/00

[52] U.S. Cl. ..................................... 127/37; 435/163; 204/157.44; 536/124; 127/1

[58] Field of Search ...................... 127/37; 204/159.44, 204/157.68, 903, 904; 435/163; 536/124, 1

[56] References Cited

U.S. PATENT DOCUMENTS 4,304,649  12/1981  Han et al. .............................. 127/37

Primary Examiner—H. M. S. Sneed
Assistant Examiner—Chung K. Pak
Attorney, Agent, or Firm—Browdy and Neimark

[57] ABSTRACT

The efficiency of enzymatic saccharification and fermentation of cellulose in a waste cellulose resource can be increased by a preliminary treatment with ionizing radiation. This irradiation of the waste cellulose resource can be accelerated by the preliminary addition of an aqueous alkali solution.

2 Claims, No Drawings

METHOD OF PRETREATMENT IN SACCHARIFICATION AND FERMENTATION OF WASTE CELLULOSE RESOURCE

This application is a continuation of application Ser. No. 778,087 filed Sept. 20, 1985, was abandoned.

BACKGROUND OF THE INVENTION

The present invention relates to a method useful in the technology of saccharification and fermentation of a waste cellulose resource.

Waste cellulose resources constitute a family of abundant non-depletive recyclable energy sources. Active efforts are being made to convert waste cellulose resources into either glucose or alcohol, and use this either as fuel or as a valuable starting material for chemical synthesis. Two methods are available for saccharifying waste cellulose resources: an enzyme saccharification process and an acid saccharification process. The first approach requires the recovery of spent acid and involves problems such as the formation of inhibitors that are deleterious to a subsequent fermentation step. Increasing attention, therefore, is being directed to the second approach which can be implemented under milder process conditions.

Waste cellulose resources such as chaff, straw, and waste wood are composites wherein cellulose, hemicellulose, and lignin are strongly bonded to one another, both physically and chemically. In order to realize efficient saccharification of the cellulose by an enzyme, the starting material must be broken down by some preliminary treatment so that good contact is established between the cellulose in the feed and the enzyme. Among preliminary treatments under study is one using a chemical such as acid or alkali to remove the lignin and other unwanted components and provide for the easy access of the anzyme to the starting material, and one that depends on mechanical grinding to provide larger surface areas. The first method uses large amounts of acids or alkalis as a sole chemical to remove lignin and other unwanted components and, therefore, is not only costly but also disadvantageous in terms of the recovery of the spent chemical. The second method is also uneconomical since it uses electric power to mechanically grind the starting material. Several reports have been written on the effects of ionizing radiation (hereunder simply referred to as radiation) on treatment of waste cellulose resources. Studies have also been made on the effects of the addition of delignifiers such as sulfuric acid, alcohols, and cadoxen, and a method has been proposed for illuminating cleaned waste cellulose resources with radiation after they have been swollen by such delignifiers. However, no report has been made of success in significantly accelerating the rate of irradiation of waste cellulose resources.

SUMMARY OF THE INVENTION

The primary object, therefore, of the present invention is to provide a method of accelerating the effect of the irradiation of waste cellulose resources as a preliminary step on the saccharification or fermentation of such resources. This object can be achieved by irradiating waste cellulose resources in the presence of an aqueous alkaline solution.

DETAILED DESCRIPTION OF THE INVENTION

The present inventors have previously found that, when waste cellulose resources are exposed to radiation, they become sufficiently fragile by radiolysis and reduce the time necessary for grinding the resources in a subsequent step. As the irradiation dose is increased, less energy is required in the subsequent mechanical grinding, but at least about 50 Mrad is necessary for making the waste resources sufficiently fragile to be easily broken down by mechanical means. The present inventors have made various studies into reducing the required radiation dose, and have found that the effect of irradiation can be accelerated by adding a small amount of an aqueous alkaline solution to the waste cellulose resources.

Th method of the present invention is effective only when waste cellulose resources are irradiated in the presence of an aqueous alkali solution. The mechanism behind the method of the invention is assumed to be as follows. When an aqueous solution of an alkali metal or alkaline earth metal hydroxide is exposed to radiation, excited nuclides and reaction intermediates are formed and react with the waste cellulose resources so as to degrade the constituents of the structure of the waste resources.

The alkali metal or alkaline earth metal salt may be used in the method of the present invention in a relatively low concentration that typically ranges from 1 to 10%, preferably from 3 to 4weight %. A sufficient amount of an aqueous solution of such an alkali metal or alkaline earth metal salt may be added to wet the surface of the waste cellulose resource, that is, 5–30 vol % of the resource. Any method may be used to add the aqueou alkaline solution to the waste cellulose resource; for example, the resource can be immersed in the aqueous alkali solution, immediately recovered therefrom, and then drained of excess alkali solution by squeezing it, in preparation for irradiation; alternatively, the waste cellulose resource can be sprayed with the aqueous alkali solution. Any radiation may be used, such as electron beams, alpha-rays, beta-rays, gamma-rays, X-rays, neutron rays, and ultraviolet rays. For practical applications that require continuous and efficient irradiation, it is preferred to shower the waste cellulose resource with accelerated electron beams as it is carried along a conveyor. As mentioned before, the amount of aqueous alkaline solution added to the waste cellulose resource is small enough to avoid any danger of substantial change in the state of the waste resource resulting from the addition of the alkali solution, so that the waste resource can be transported smoothly on a feeder.

The addition of the aqueous alkali solution accelerates the irradiation of the waste cellulose resource, so the radiation dose necessary for facilitating the subsequent mechanical grinding can be at low levels ranging from 5 to 30 Mrad, preferably 10 Mrad. The waste cellulose resource may be irradiated at roo temperature. The material that can be treated by the method of the present invention may be any of the cellulose-containing waste materials such as chaff, straw, bagasse, waste paper, and waste wood such as sawdust. The preferred alkali components of the aqueous solution, which is to be added to the waste cellulose resource, are hydroxides of alkali metals and alkaline earth metals.

The aqueous alkali solution is preferably added to the waste cellulose resource before the latter is exposed to radiation, and no accelerated irradiation is realized in the absence of the aqueous alkali solution. Since only a small quantity of aqueous alkali solution is added, the irradiated waste cellulose resource may be slightly dried in air and mechanically ground in preparation for subsequent saccharification. If desired, the irradiated waste cellulose resource may be immediately subjected to saccharification. The waste cellulose resource after irradiation contains small amounts of alkali, but in most cases no neutralization is necessary since enzymatic saccharification is generally performed under acidic conditions at a pH of 4–5. If desired, the waste cellulose resource may be neutralized by the addition of a small amount of an acetate buffer solution prior to the saccharification. As will be apparent from the foregoing description, the method of the present invention is simple to operate since it is based on the irradiation of waste cellulose resources in the presence of a small amount of an aqueous solution with a low concentration of alkali.

The following examples are provided to further illustrate the advantages of the method of the present invention.

EXAMPLE 1

Chaff (1,000 cm$^3$) was sprayed with 150 ml of 3% aqueous NaOH solution and then mixed so that a uniform coating of the aqueous NaOH solution was formed on the surfaces of the chaff. The chaff was then put into a polyethylene bag and a layer of chaff 2–3 cm thick was given 10 Mrad exposure of electron beams from an accelerator. The irradiated chaff was dried in air and divided into fine particles with a pulverizer type of grinder. The resultant powder was mixed with 0.1M acetate buffer solution to make 10 ml of 10% substrate solution. After pipetting a drop of acetic acid, 100 mg of cellulase was added to the substrate solution which was saccharified by shaking at 40° C. for 48 hours. As a control, chaff was exposed to electron beams without the addition of 2% aqueous NaOH solution, then saccarified under the same conditions as described above. The glucose level in the sample irradiated after the addition of the NaOH solution was 2.1%, whereas the control that was irradiated without addition of the NaOH solution had a glucose level of 0.8%.

EXAMPLE 2

Bagasse (1,000 cm$^3$) was sprayed with 100 ml of 2% aqueous KOH solution and given a 20 Mrad exposure of electron beams from an accelerator, in the same way as in Example 1. The irradiated bagasse was immediately mixed with 0.1M acetate buffer solution to make a 10% substrate solution. A predetermined amount of this solution was put into an Erlenmeyer flask, and, after the addition of 1% cellulase, the bagasse in the solution was saccharified by shaking at 40° C. for 48 hours. As a control, bagasse was exposed to electron beams without the addition of KOH solution, and saccharified as described above. The glucose levels in the KOH-treated sample and the control were 3.5% and 0.7%, respectively.

EXAMPLE 3

Shreds of rice hulls (1,000 cm$^3$) were sprayed with 2% aqueous NaOH solution and mixed together. The mixture was put into a polyethylene bag and irradiated with gamma-rays from $^{60}$Co for 5 hours at a dose rate of $2 \times 10^6$ R/hr (10 Mrad). The irradiated hulls were dried in air and ground into particles in a ball mill for 24 hours. A predetermined amount of the powder was mixed with 0.1M acetate buffer solution to make a 20% substrate solution, which was saccharified with 1% cellulase by shaking at 40° C. for 48 hours. As a control, shreds of rice hulls were irradiated with gamma-rays from $^{60}$Co without the addition of NaOH, ground into particles, and saccharified with cellulase as described above. The glucose levels in the NaOH-treated sample and the control were 3.4% and 1.3%, respectively.

What is claimed is:

1. A method for saccharification of waste cellulosic resource to produce glucose comprising:
    (1) subjecting said cellulosic resource to a preliminary treatment comprising:
    contacting the surface of said cellulosic resource with a sufficient amount of an aqueous solution to wet the surface of said cellulosic resource, said aqueous solution selected from the group consisting of 1 to 4% by weight solutions of alkali metal and alkaline earth metal hydroxides;
    irradiating the resulting wetted cellulosic resource with ionizing ratiation at a radiation dosage ranging from 5 Mrad to 20 Mrad; and
    (2) saccharifying ensymatically the resultant cellulosic resource.

2. The process of claim 1 wherein the resultant irradiated cellulosic resource is mechanically ground prior to said saccharifying.

* * * * *